(12) United States Patent
Yatabe

(10) Patent No.: US 11,136,519 B2
(45) Date of Patent: *Oct. 5, 2021

(54) COATING AGENT AND MEDICAL INSTRUMENT SURFACE-TREATED WITH SAID COATING AGENT

(71) Applicant: TERUMO KABUSHIKI KAISHA, Tokyo (JP)

(72) Inventor: Teruyuki Yatabe, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/452,827

(22) Filed: Jun. 26, 2019

(65) Prior Publication Data

US 2019/0316055 A1 Oct. 17, 2019

Related U.S. Application Data

(63) Continuation of application No. PCT/JP2017/040079, filed on Nov. 7, 2017.

(30) Foreign Application Priority Data

Dec. 27, 2016 (JP) .............................. JP2016-253828

(51) Int. Cl.
*C10M 107/50* (2006.01)
*C09D 183/04* (2006.01)
*A61L 31/10* (2006.01)
*C10M 177/00* (2006.01)
*C10N 40/00* (2006.01)
*C10N 50/08* (2006.01)

(52) U.S. Cl.
CPC ........... *C10M 107/50* (2013.01); *A61L 31/10* (2013.01); *C09D 183/04* (2013.01); *C10M 177/00* (2013.01); *C10M 2229/0415* (2013.01); *C10M 2229/0525* (2013.01); *C10N 2040/50* (2020.05); *C10N 2050/08* (2013.01)

(58) Field of Classification Search
CPC ...... C10M 2219/04; C10M 2219/0405; C10M 2219/041; C10M 2219/0415; C10M 2219/052; C10M 2219/0525; C10M 107/50
See application file for complete search history.

(56) References Cited

U.S. PATENT DOCUMENTS 5,290,545 A * 3/1994 Halloran ................ A61K 8/891
424/70.122
6,015,398 A 1/2000 Arimatsu et al.
10,556,041 B2 * 2/2020 Yatabe ..................... A61L 31/00
(Continued)

FOREIGN PATENT DOCUMENTS

CN 104105765 A 10/2014
CN 104284967 A 1/2015
(Continued)

OTHER PUBLICATIONS

An English Translation of the International Search Report (Form PCT/ISA/210) and the Written Opinion of the International Searching Authority (Form PCT/ISA/237) dated Jan. 23, 2018, by the Japanese Patent Office in corresponding International Application No. PCT/JP2017/040079. (6 pages).
Naim et al., "The Effect of Molecular Weight and Gel Preparation on Humoral Adjuvancy of Silicone Oils and Silicone Gels," Immunological Investigations, a Journal of Molecular and Cellular Immunology, Jul. 7, 2009, vol. 24, 1995, No. 3, pp. 537-547.
(Continued)

*Primary Examiner* — Marc S Zimmer
(74) *Attorney, Agent, or Firm* — Buchanan Ingersoll & Rooney PC

(57) ABSTRACT

Disclosed is a coating agent that contains a polyorganosiloxane (1) represented by the following general formula (1), a polydiorganosiloxane (2) represented by the following general formula (2), and either one of an amino group-containing polyorganosiloxane (3) represented by the following general formula (3) and a hydroxy group-containing polyorganosiloxane (4) represented by the following general formula (4). A coating agent having improved piecing properties and a medical instrument (for example, a needle) surface-treated (coated) with the coating agent are provided.

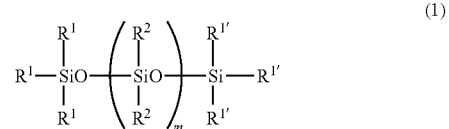

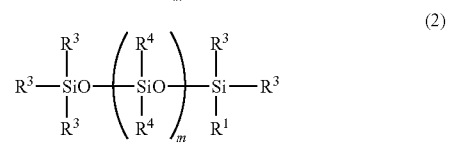

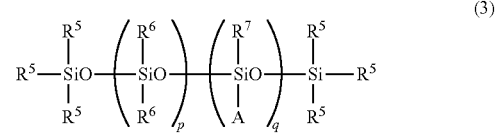

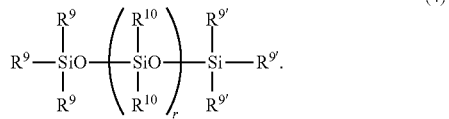

18 Claims, 2 Drawing Sheets

(56) References Cited

U.S. PATENT DOCUMENTS

| | | | |
|---|---|---|---|
| 2001/0021832 A1 | 9/2001 | Numao et al. | |
| 2013/0122204 A1* | 5/2013 | Evans | C08J 3/05 427/372.2 |
| 2013/0122314 A1 | 5/2013 | Ou | |
| 2015/0322366 A1 | 11/2015 | Santucci-Aribert | |
| 2015/0337088 A1* | 11/2015 | Chevalier | C08L 27/18 523/435 |

FOREIGN PATENT DOCUMENTS

| | | | |
|---|---|---|---|
| JP | H07178159 | A | 7/1995 |
| JP | H10309316 | A | 11/1998 |
| JP | 2001190654 | A | 7/2001 |
| JP | 2004313229 | A | 11/2004 |
| WO | 2004/083348 | A2 | 9/2004 |
| WO | 2016013528 | A1 | 1/2016 |
| WO | 2017002599 | A1 | 1/2017 |

OTHER PUBLICATIONS

The extended European Search Report dated Jul. 21, 2020, by the European Patent Office in corresponding European Patent Application No. 17886321.3-1107. (8 pages).
International Search Report (PCT/ISA/210) dated Jan. 23, 2018, by the Japanese Patent Office as the International Searching Authority for International Application No. PCT/JP2017/040079.
Notification of the First Office Action issued from the Chinese Patent Office dated Dec. 28, 2020 in corresponding Chinese Patent Application No. 2017800802131. (17 pages).

* cited by examiner

COATING AGENT AND MEDICAL INSTRUMENT SURFACE-TREATED WITH SAID COATING AGENT

CROSS-REFERENCES TO RELATED APPLICATIONS

This application is a continuation of International Application No. PCT/JP2017/040079 filed on Nov. 7, 2017, and claims priority to Japanese Application No. 2016-253828 which was filed on Dec. 27, 2016, the entire contents of both of which are incorporated herein by reference.

TECHNICAL FIELD

Disclosed are a coating agent and a medical instrument surface-treated with the coating agent.

BACKGROUND DISCUSSION

Patients suffering from diseases and healthy persons undergo various medical activities, such as medical examination. For example, injection is used for patients suffering from diseases for the purpose of drug infusion for treatment, anesthesia at an operation, or the like. In addition, even a healthy person often experiences injection in blood donation, vaccination, or the like. However, injection gives great distress, such as pain at puncture or discomfort at drug infusion, to patients and healthy persons. Accordingly, for the purpose of pain relief, various studies have been made on the tip shape of an injection needle, a coating agent on an injection needle surface, and the like. Among them, silicone is used as a coating agent on an injection needle surface. Such silicone coating agents impart lubricity to an injection needle to reduce friction at puncture. Thus, an injection needle coated with a silicone coating agent relieves a pain at injection. For example, JP-A-7-178159 proposes a silicone coating agent that contains an amino group-containing polyorganosiloxane and a polydiorganosiloxane at a specific mixing ratio. An injection needle coated with the coating agent shows excellent piercing properties.

SUMMARY

However, an injection needle coated with the coating agent disclosed in JP-A-7-178159 does not avoid giving pain to a subject, such as a patient, and it is beneficial to improve the piercing properties.

In addition, a needle coated with a silicone coating agent is used in multiple punctures in some cases. For example, a needle treated with a silicone coating is sometimes used in injection of a patient after piercing a cap of a drug bottle to suck a drug solution. In addition, an infusion spike treated with a silicone coating sometimes repeatedly pierces different infusion bags in replacing an infusion bag. In such cases, there is a problem in that a film of the coating agent is separated from a needle surface, increasing friction (puncture resistance) in use to give a patient pain. Thus, it is also beneficial to further enhance durability (suppression and prevention of separation of a coating).

Accordingly, aspects of the present disclosure were made in view of the above circumstances, and an exemplary object of the present disclosure is to provide a coating agent having improved piercing properties and a medical instrument (for example, a needle) surface-treated (coated) with the coating agent. In addition, another object of the present disclosure is to provide a coating agent having enhanced durability and a medical instrument (for example, a needle) surface-treated (coated) with the coating agent.

For example, the above problem can be ameliorated or solved by a coating agent that contains two polyorganosiloxanes with different polymerization degrees and an amino group-containing polyorganosiloxane or a hydroxy group-containing polyorganosiloxane.

For example, the above objects can be achieved by a coating agent that contains:

(1) a polyorganosiloxane (1) represented by the following general formula (1):

[Chem. 1]

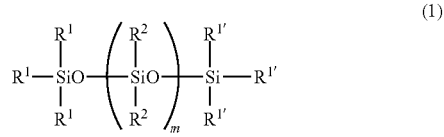

wherein each $R^1$ and each $R^2$ independently represents a monovalent hydrocarbon group, each $R^{1'}$ independently represents a monovalent hydrocarbon group or a hydroxy group (—OH group), and m is an integer of 1,500 to 30,000;

(2) a polydiorganosiloxane (2) represented by the following general formula (2):

[Chem. 2]

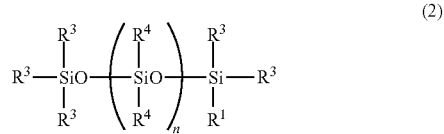

wherein each $R^3$ and each $R^4$ independently represents a monovalent hydrocarbon group, and n is an integer of 8 to 1,000; and one of (3) an amino group-containing polyorganosiloxane (3) containing at least one amino group per molecule represented by the following general formula (3):

[Chem. 3]

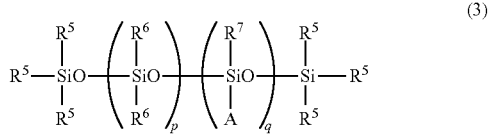

wherein each $R^5$ independently represent a monovalent hydrocarbon group or an —OR8 group, wherein each R8 independently represents a substituted or unsubstituted monovalent hydrocarbon group having 1 to 4 carbon atoms, each $R^6$ and each $R^7$ independently represents a monovalent hydrocarbon group, each A independently represents an amino group-containing group, p:q=5 to 100:1, and q is an integer of 1 to 100, or (4) a hydroxy group-containing polyorganosiloxane (4) represented by the following general formula (4):

[Chem. 4]

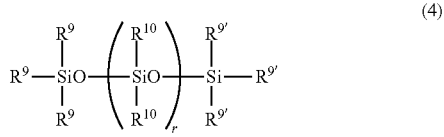

(4)

wherein each $R^9$ and each $R^{9'}$ independently represents a monovalent hydrocarbon group or a hydroxy group (—OH), provided that at least one $R^9$ is a hydroxy group (—OH) and at least one $R^{9'}$ is a hydroxy group (—OH), each R10 independently represents a monovalent hydrocarbon group, and r is an integer of 1,000 to 30,000.

DETAILED DESCRIPTION

Figure 1A:
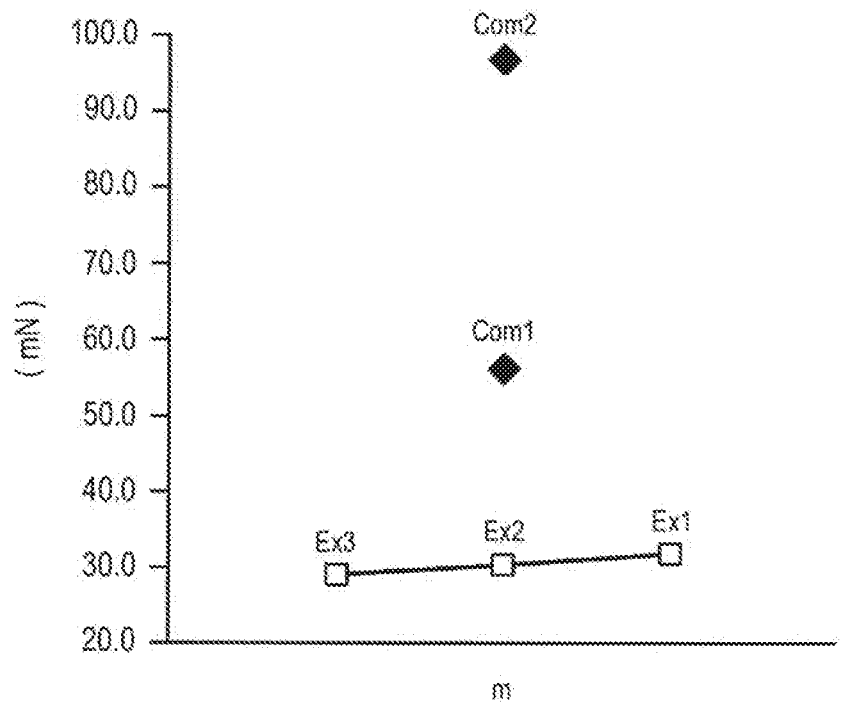
FIG. 1A is a graph showing initial (zero-puncture) puncture resistances (sliding resistance values (mN)) of needles surface-treated by heating with coating agents of Examples 1 to 3 (Ex. 1 to 3) and Comparative Examples 1 to 2 (Com. 1 to 2), according to exemplary embodiments.

Exemplary embodiments of the present disclosure will be described below. An exemplary coating agent of the present disclosure contains:

(1) a polyorganosiloxane (1) represented by the following general formula (1):

[Chem. 5]

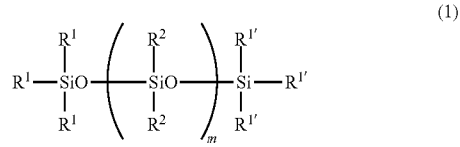

(1)

wherein each $R^1$ and each $R^2$ independently represents a monovalent hydrocarbon group, each $R^{1'}$ independently represents a monovalent hydrocarbon group or a hydroxy group (—OH group), and m is an integer of 1,500 to 30,000;

(2) a polydiorganosiloxane (2) represented by the following general formula (2):

[Chem. 6]

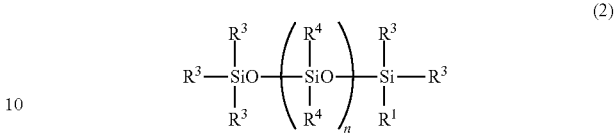

(2)

wherein each $R^3$ and each $R^4$ independently represents a monovalent hydrocarbon group, and n is an integer of 8 to 1,000; and one of (3) an amino group-containing polyorganosiloxane (3) containing at least one amino group per molecule represented by the following general formula (3):

[Chem. 7]

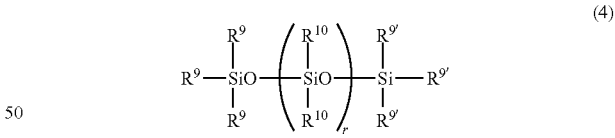

(3)

wherein each $R^5$ independently represents a monovalent hydrocarbon group or an —$OR^8$ group, wherein each $R^8$ independently represents a substituted or unsubstituted monovalent hydrocarbon group having 1 to 4 carbon atoms, each $R^6$ and each $R^7$ independently represents a monovalent hydrocarbon group, each A independently represents an amino group-containing group, p:q=5 to 100:1, and q is an integer of 1 to 100, or (4) a hydroxy group-containing polyorganosiloxane (4) represented by the following general formula (4):

[Chem. 8]

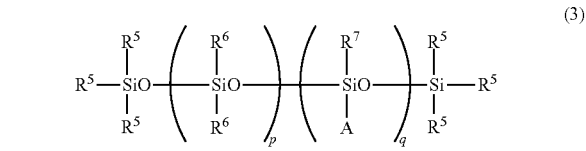

(4)

wherein each $R^9$ and each $R^{9'}$ independently represents a monovalent hydrocarbon group or a hydroxy group (—OH), provided that at least one $R^9$ is a hydroxy group (—OH) and at least one $R^{9'}$ is a hydroxy group (—OH), each $R^{10}$ independently represents a monovalent hydrocarbon group, and r is an integer in a range of 1,000 to 30,000. A coating agent having the above structure can be excellent in lubricity. Thus, a needle surface-treated with the coating agent can reduce friction (puncture resistance or piercing resistance) at puncture and can improve piercing properties (for example, initial piercing properties). Furthermore, for example, since the coating agent forms a strong film and is also excellent in adhesiveness to a base material (for example, a medical instrument, such as a needle, catheter, or cannula) surface, the coating agent can suppress or prevent separation of a coating from a base material and thus can be excellent in durability.

As used herein, the polyorganosiloxane (1) represented by the general formula (1) is referred to as "polyorganosiloxane (1)", the polydiorganosiloxane (2) represented by the general formula (2) is as "polydiorganosiloxane (2)" or "polyorganosiloxane (2)", and an amino group-containing polyorganosiloxane (3) containing at least one amino group per molecule represented by the general formula (3) is as "amino group-containing polyorganosiloxane (3)" or "polyorganosiloxane (3)", and the hydroxy group-containing polyorganosiloxane (4) represented by the general formula (4) is as "hydroxy group-containing polyorganosiloxane (4)" or "polyorganosiloxane (4)".

An exemplary coating agent is characterized by:

(a) containing the polyorganosiloxane (1) with a high polymerization degree and the polydiorganosiloxane (2) with a low polymerization degree; and (b) further containing, in addition to the above components, either one of the amino group-containing polyorganosiloxane (3) or the hydroxy group-containing polyorganosiloxane (4).

That is, the coating agent contains the polyorganosiloxane (1), the polydiorganosiloxane (2), and the amino group-containing polyorganosiloxane (3), or contains the polyorganosiloxane (1), the polydiorganosiloxane (2), and the hydroxy group-containing polyorganosiloxane (4).

The coating agent can reduce friction on a base material and thus can be excellent in piercing properties (for example, initial piercing properties). In addition, since the coating agent can be excellent in film formability and excellent in adhesiveness to a base material (for example, needle, catheter, cannula, three-way stopcock) surface, the separation of a surface-treating body (film) of the coating agent from a base material can suppressed or prevented, leading to excellent durability. In addition, the reason why the above exemplary effects can be achieved is explained as follows. The present disclosure is not limited by the following explanation.

The present inventor has earnestly studied about further improvement in the piercing properties of the coating agent disclosed in JP-A-7-178159 as mentioned above. The present inventor has also earnestly studied about enhancement in durability of the coating agent on a base material. As a result, the present inventor has found that the characteristics (a) and (b) as described above can be effective means.

As described above as the characteristic (b), the coating agent contains either one of the amino group-containing polyorganosiloxane (3) or the hydroxy group-containing polyorganosiloxane (4). Here, the amino group-containing polyorganosiloxane (3) and the hydroxy group-containing polyorganosiloxane (4) are bound to a base material through the amino group and the hydroxy groups at both the ends, respectively. Then, the amino group or the hydroxy groups are bonded to (form a relatively long crosslinking structure with) the base material (for example, a hydroxy group on a surface of a metal base material), and the polyorganosiloxane moiety further forms a network structure to form a film. In this way, the amino group-containing polyorganosiloxane (3) and the hydroxy group-containing polyorganosiloxane (4) contribute to the adhesiveness to a base material and the formability of a film.

For example, as described above as the characteristic (a), the coating agent further contains the polyorganosiloxane (1) with a high polymerization degree (m in the general formula (1) is an integer of 1,500 to 30,000) and the polydiorganosiloxane (2) with a low polymerization degree (n in the general formula (2) is an integer of 8 to 1,000).

For example, the polyorganosiloxane (1) with a high polymerization degree not only contributes to the formation of a film by the long molecular chain (polyorganosiloxane moiety), but also imparts lubricity (improves piercing properties) by the polyorganosiloxane moiety. Furthermore, the polydiorganosiloxane (2) with a low polymerization degree can improve the piercing properties by the polydiorganosiloxane moiety.

For example, the polyorganosiloxane (1) and the polydiorganosiloxane (2) exist so as to permeate (so that the molecular chains are entangled in) the network of a film formed of the amino group-containing polyorganosiloxane (3) or the hydroxy group-containing polyorganosiloxane (4). Then, these components can ooze from the network of the film when the friction force is exerted, enhancing lubricity (improving piercing properties).

For example, the polyorganosiloxane (1) with a high polymerization degree constitutes a part of a film, while being able to ooze when a friction force is exerted. For example, the polyorganosiloxane (1) with a high polymerization degree is entangled with the amino group-containing polyorganosiloxane (3) or the hydroxy group-containing polyorganosiloxane (4) more strongly as compared with the polyorganosiloxane (2) with a low polymerization degree. For example, under a smaller friction force, the polyorganosiloxane (2) mainly oozes, and under a larger friction force, the polyorganosiloxane (1) also oozes in addition to the polyorganosiloxane (2). For example, a medical tool (for example, needle) surface-treated with the coating agent can exhibit excellent lubricity regardless of whether the friction force is large or small. For example, a film containing the polyorganosiloxane (1) has higher film strength than a film not containing the polyorganosiloxane (1) due to the high polymerization degree. For example, in a medical tool (for example, needle) surface-treated with the coating agent, separation of the coating agent due to friction can be suppressed or prevented due to the film strength, and the durability can be enhanced. Accordingly, the polyorganosiloxane (1) can partially contribute to the film formability, while contributing enhancement in the lubricity. Accordingly, the coating agent can reduce friction on a base material and is excellent in the piercing properties.

Furthermore, the coating agent contains the amino group-containing polyorganosiloxane (3) or the hydroxy group-containing polyorganosiloxane (4) that can contribute to film formability as described in the characteristic (b), which can enhance the strength of a film of the coating agent. For example, due to the strength of the film by these components, the polyorganosiloxane (1) and the polydiorganosiloxane (2) can be held in a film and elimination of the polyorganosiloxane (1) and the polydiorganosiloxane (2) due to friction can be suppressed or prevented, enhancing the durability.

As described above, the coating agent can exhibit enhanced lubricity (in particular, initial piercing properties) when applied on a base material. In addition, the coating agent can exhibit enhanced durability when applied on a base material. Furthermore, the coating agent can achieve a good balance of the lubricity, adhesiveness, and film formability when applied on a base material. Hence, the coating agent can be suitably used on a medical instrument in which the features as described above are desired, for example, a needle, such as an injection needle. That is, the present disclosure also provides a medical instrument (for example, a medical instrument that generates friction at insertion into a living body, for example, needle, catheter, or cannula) surface-treated with the coating agent.

With such a medical instrument, for example, separation of a film (coating agent) from a surface of the medical instrument can be suppressed even after multiple uses. Since a high lubricity can thus be maintained, the friction (puncture resistance) in use can be reduced, resulting in effective relief of pain experienced by patients. Furthermore, with the coating agent, separation of a film from a medical instrument (base material) surface can be suppressed or prevented. Thus, in a medical tool (for example, needle, catheter, cannula, or three-way stopcock) surface-treated with the coating agent, separation of a surface-treating body (film) of the coating agent from the base material can be suppressed or prevented, and the lubricity can be maintained for a long period of time (excellent durability). Hence, when a needle surface-treated with the coating agent sequentially pierces different infusion bags, contamination in an infusion bag by foreign substances (film separated piece) can be suppressed or prevented, which is exemplary from the safety viewpoint. In addition, for example, although a three-way stopcock is not inserted in a living body, slidability of a moving part of the three-way stopcock can be maintained.

Exemplary embodiments of the present disclosure will be described below. As used herein, "X to Y" that represents any range means inclusion of X and Y, and refers to "X or more and Y or less". In addition, unless otherwise specified, operation and measurement of physical properties are performed under conditions at room temperature (20 to 25° C.) and at a relative humidity of 40 to 50% RH.

Although an embodiment in which the medical instrument is a needle is described in detail below, the present disclosure is not limited to the following embodiment. For example, other medical instruments, such as a catheter, can be applied in the same manner.

[Polyorganosiloxane (1)]

The polyorganosiloxane (1) is represented by the following general formula (1).

[Chem. 9]

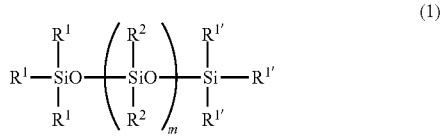

(1)

For example, when plural structural units of the formula: —Si(R²)₂O— are present, the structural units may be the same or different. In addition, the coating agent may contain one polyorganosiloxane (1) alone or two or more polyorganosiloxanes (1).

The polyorganosiloxane (1) can be a polyorganosiloxane with a relatively high polymerization degree (m). As is shown in the structure, the polyorganosiloxane (1) can be a polyorganosiloxane that has a triorganosilyl group at both the ends of the molecular chain and has no amino group in the molecule or a polyorganosiloxane that has a triorganosilyl group at one end of the molecular chain, has a hydroxy (organo)silyl group at the other end, and has no amino group in the molecule.

The polyorganosiloxane (1) can form a part of a film by the organosiloxane moiety, and can impart lubricity to a film (network structure) formed of the amino group-containing polyorganosiloxane (3) or the hydroxy group-containing polyorganosiloxane (4). Thus, a film formed of the coating agent containing the polyorganosiloxane (1) can exhibit high lubricity (piercing easiness, piercing resistance reduction effect), for example at the initial piercing when a large friction force is exerted. In addition, since the polyorganosiloxane (1) has a high polymerization degree, a film formed of the coating agent can have high film strength. Therefore, a film excellent in durability can be formed.

In the general formula (1), R¹ represents a monovalent hydrocarbon group and R¹' represents a monovalent hydrocarbon group or a hydroxy group (—OH). Here, R¹ and R¹' may be the same or different. In addition, in —Si(R¹)₃, each R¹ may be the same or different. Similarly, in —Si(R¹)₃, each R¹' may be the same or different.

Here, as described above, the general formula (1) can include a form where both the ends are a monovalent hydrocarbon group (that is, all of R¹'s and R¹'s are each a monovalent hydrocarbon group) and a form where one end is a monovalent hydrocarbon group and the other end contains a hydroxy group (that is, each R¹ is a monovalent hydrocarbon group and at least one R¹' is a hydroxy group). In view of the effect of enhancing lubricity (piercing properties), the polyorganosiloxane (1) can have the former form (that is, all the R¹'s and R¹'s are each a monovalent hydrocarbon group). That is, each R¹' in the general formula (1) can be a monovalent hydrocarbon group. For example, each R¹ and each R¹' can be a monovalent hydrocarbon group. In the latter form (that is, R¹'s are each a monovalent hydrocarbon group and at least one R¹' is a hydroxy group), one end can be bonded to a base material via a hydroxy group and such an area that the polyorganosiloxane moiety can move freely can be limited. In contrast, in the former form, for example, neither end is fixed to a base material, and therefore the polyorganosiloxane moiety can move freely. As a result, when a friction force is exerted, the polyorganosiloxane (1) can easily ooze, tending to enhance the lubricity (piercing properties).

On the other hand, in view of the effect of enhancing durability of a film, at least one R¹' can be a hydroxy group. With such a form, the hydroxy group can be bonded to a base material, tending to enhance durability of the film.

Examples of the monovalent hydrocarbon groups as R¹ and R¹' include, but are not limited to, a linear or branched alkyl group having 1 to 24 carbon atoms, a linear or branched alkenyl group having 2 to 24 carbon atoms, a cycloalkyl group having 3 to 9 carbon atoms, and an aryl group having 6 to 30 carbon atoms.

Examples of linear or branched alkyl groups having 1 to 24 carbon atoms include, but are not limited to, a methyl group, an ethyl group, an n-propyl group, an isopropyl group, an n-butyl group, an isobutyl group, a sec-butyl group, a tert-butyl group, an n-pentyl group, an isopentyl group, a tert-pentyl group, a neopentyl group, a 1,2-dimethylpropyl group, an n-hexyl group, an isohexyl group, a 1,3-dimethylbutyl group, a 1-isopropylpropyl group, a 1,2-dimethylbutyl group, an n-heptyl group, a 1,4-dimethylpentyl group, a 3-ethylpentyl group, a 2-methyl-1-isopropylpropyl group, a 1-ethyl-3-methylbutyl group, an n-octyl group, a 2-ethylhexyl group, a 3-methyl-1-isopropylbutyl group, a 2-methyl-1-isopropyl group, a 1-t-butyl-2-methylpropyl group, an n-nonyl group, a 3,5,5-trimethylhexyl group, an n-decyl group, an isodecyl group, an n-undecyl group, a 1-methyldecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group, an n-heneicosyl group, an n-docosyl group, an n-tricosyl group, and an n-tetracosyl group. Examples of linear or branched alkenyl groups having 2 to 24 carbon atoms include, but are not limited to, a vinyl group, a 1-propenyl group, a 2-propenyl group (allyl group), an isopropenyl group, a 1-butenyl group, a 2-butenyl group, a 3-butenyl group, a 1-pentenyl group, a 2-pentenyl group, a 3-pentenyl group, a 1-hexenyl group, a 2-hexcenyl group, a 3-hexenyl group, a 1-heptenyl group, a 2-heptenyl group, a 5-heptenyl group, a 1-octenyl group, a 3-octenyl group, a 5-octenyl group, a dodecenyl group, and an octadecenyl group. Examples of cycloalkyl groups having 3 to 9 carbon atoms include, but are not limited to, a cyclopropyl group, a cyclobutyl group, a cyclopentyl group, a cyclohexyl group, a cycloheptyl group, and a cyclooctyl group. Examples of aryl groups having 6 to 30 carbon atoms include, but are not limited to, a phenyl group, a biphenyl group, a terphenyl group, a pentalenyl group, an indenyl group, a naphthyl group, an azulenyl group, a heptalenyl group, a biphenylenyl group, a fluorenyl group, an acenaphthylenyl group, a preiadenyl group, an acenaphthenyl group, a phenalenyl group, a phenanthryl group, an anthryl group, a fluoranthenyl group, an acephenanthrylenyl group, an aceanthrylenyl group, a triphenylenyl group, a pyrenyl group, chrysenyl group, and a naphthacenyl group.

For example, among them, from the viewpoint of a further effect of enhancing lubricity and of the compatibility with solvents, each $R^1$ and each $R^{1'}$ can be a linear or branched alkyl group having 1 to 16 carbon atoms, for example, a linear or branched alkyl group having 1 to 8 carbon atoms, for example, a linear or branched alkyl group having 1 to 4 carbon atoms, for example, a methyl group. The "compatibility" refers to mutual solubility of different kinds of molecules and means the easiness of mixing at the molecular level.

In the general formula (1), $R^2$ represents a monovalent hydrocarbon group. Here, an $R^2$ present in one structural unit may be the same or different. In addition, when plural structural units are present, the structural units may be the same or different. The monovalent hydrocarbon groups as $R^2$s have the same definition as in $R^1$s and $R^{1'}$s described above, and thus the explanation is omitted here. From the viewpoint of a further effect of enhancing lubricity and durability and of the compatibility with solvents, each $R^2$ can be a linear or branched alkyl group having 1 to 16 carbon atoms, for example, a linear or branched alkyl group having 1 to 8 carbon atoms, for example, a linear or branched alkyl group having 1 to 4 carbon atoms, for example, a methyl group.

That is, in an exemplary embodiment, in the general formula (1), each $R^1$ and each $R^{1'}$ is independently a linear or branched alkyl group having 1 to 4 carbon atoms and each $R^2$ is independently a linear or branched alkyl group having 1 to 4 carbon atoms. In addition, in an exemplary embodiment, in the general formula (1), each $R^1$ and each $R^{1'}$ is a methyl group, and each $R^2$ is a methyl group.

In addition, m is an integer in a range of 1,500 to 30,000, for example, an integer in a range of 2,000 to 20,000, for example, an integer in a range of 3,000 to 15,000, for example, an integer in a range of 3,500 to 10,000. With m in the above range, a sufficient effect of enhancing lubricity (piercing properties) can be obtained by the polyorganosiloxane (1). The molecular weight of the polyorganosiloxane (1) is not limited. The weight average molecular weight can be in a range of 100,000 to 2,000,000, for example, 150,000 to 1,500,000, for example, 200,000 to 1,000,000, for example, 250,000 to 800,000. As used herein, the weight average molecular weight means a value obtained from a measurement result of gel filtration chromatography (GPC) by a calibration curve method with polystyrene used as a standard. In addition, as used herein, the polymerization degree (m in the general formula (1), n in the general formula (2), p and q in the general formula (3), r in the general formula (4), etc.) can be calculated on the basis of the weight average molecular weight mentioned above and the structure (repeating unit structure) of the polyorganosiloxanes (1) to (4). The structure (repeating unit structure) of the polyorganosiloxanes (1) to (4) can be specified by $^1$H-NMR or other techniques.

Furthermore, m can satisfy the following in the relationship with n in the general formula (2) as described in detail later. That is, the ratio of m in the general formula (1) to n in the general formula (2) (m/n) can be in a range of 5:1 to 400:1.

With a ratio in the above range, the effect of enhancing the lubricity (piercing properties) by the polyorganosiloxane (1) and the polydiorganosiloxane (2) can be obtained. In addition, from the viewpoint of enhancing durability at the same time, the ratio (m/n) can be in a range of 50:1 to 300:1, for example, 100:1 to 250:1, for example, 100:1 to 200:1.

Examples of the polyorganosiloxane (1) include polydimethylsiloxane, polydiethylsiloxane, polydipropylsiloxane, polydiisopropylsiloxane, polymethylethylsiloxane, polymethylpropylsiloxane, polymethylisopropylsiloxane, polyethylpropylsiloxane, and polyethylisopropylsiloxane. Among them, in view of lubricity (piercing properties) and the like, polydimethylsiloxane and polydiethylsiloxane are exemplary, and polydimethylsiloxane is exemplary.

The content of the polyorganosiloxane (1) is not limited. In view of a better balance of the lubricity, adhesiveness, and film formability, the content of the polyorganosiloxane (1) based on the total mass of the polyorganosiloxane (1), the polydiorganosiloxane (2), and the amino group-containing polyorganosiloxane (3) or the hydroxy group-containing polyorganosiloxane (4) can be 2.0 to 6.0% by mass, for example, 2.4 to 5.5% by mass, for example, 3.0 to 4.5% by mass, for example, 3.2 to 4.1% by mass. With such a content, the lubricity (piercing easiness, piercing resistance reduction effect) and durability can be enhanced more effectively. When two or more polyorganosiloxanes (1) are contained, the content means the total content of the polyorganosiloxanes (1).

The coating agent can contain the polyorganosiloxane (1) in such an amount that the ratio by mass to the polydiorganosiloxane (2) is 0.01 to 0.15. With such a content, the lubricity (piercing easiness, piercing resistance reduction effect) and durability can be enhanced more effectively. In view of a further effect of enhancing lubricity and durability, the ratio by mass of the polyorganosiloxane (1) to the polydiorganosiloxane (2) can be in a range of 0.02 to 0.14, for example, 0.03 to 0.10, for example, 0.04 to 0.07, for example, 0.05 to 0.06.

[Polydiorganosiloxane (2)]

The polydiorganosiloxane (2) is represented by the following general formula (2).

[Chem. 10]

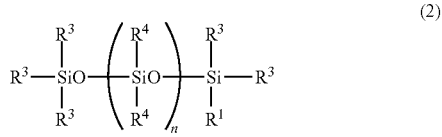

For example, when plural structural units of the formula: —Si(R$^4$)$_2$O— are present, the structural units may be the same or different. In addition, the coating agent may contain one polydiorganosiloxane (2) alone or two or more polydiorganosiloxanes (2).

The polydiorganosiloxane (2) can be a polydiorganosiloxane with a relatively low polymerization degree (n). As is shown in the above structure, the polydiorganosiloxane (2) can have a triorganosilyl group at both the ends of the molecular chain and can contain no amino group in the molecule, and can contain substantially no hydroxy group and no hydrolyzable group in the molecule.

The polydiorganosiloxane (2) can impart lubricity to a film formed of the amino group-containing polyorganosiloxane (3) or the hydroxy group-containing polyorganosiloxane (4) by the organosiloxane moiety therein. For example, due to the presence of the polydiorganosiloxane (2), the formed film can exhibit high lubricity (piercing easiness, piercing resistance reduction effect) especially at the initial piercing when a small friction force is exerted.

In the general formula (2), each R$^3$ and each R$^4$ represents a monovalent hydrocarbon group. For example, plural R$^3$s may be the same or different. For example, plural R$^4$s may be the same or different. The monovalent hydrocarbon groups as R$^3$s and R$^4$s have the same definition as that in the general formula (1), and thus the explanation is omitted here. Among them, from the viewpoint of a further effect of enhancing lubricity, the monovalent hydrocarbon groups as R$^3$s and R$^4$s can be a linear or branched alkyl group having 1 to 16 carbon atoms, for example, a linear or branched alkyl group having 1 to 8 carbon atoms, for example, a linear or branched alkyl group having 1 to 4 carbon atoms, for example, a methyl group.

That is, in an exemplary embodiment, each R$^3$ and each R$^4$ in the general formula (2) is independently a linear or branched alkyl group having 1 to 4 carbon atoms. In addition, in an exemplary embodiment, each R$^3$ and each R$^4$ in the general formula (2) is a methyl group.

In the general formula (2), n is an integer in a range of 8 to 1,000, for example, an integer in a range of 10 to 200, for example, an integer in a range of 20 to 100, for example, an integer in a range of 30 to 50. With n in the above range, a sufficient effect of enhancing lubricity (piercing properties) can be obtained by the polydiorganosiloxane (2), and friction on base material (puncture resistance) can be further reduced. For example, the molecular weight of the polydiorganosiloxane (2) is not limited. The weight average molecular weight can be 500 to 7,000, for example, 1,500 to 5,000, for example, 2,000 to 4,000.

Examples of the polydiorganosiloxane (2) include polydimethylsiloxane, polydiethylsiloxane, polydipropylsiloxane, polydiisopropylsiloxane, polymethylethylsiloxane, polymethylpropylsiloxane, polymethylisopropylsiloxane, polyethylpropylsiloxane, and polyethylisopropylsiloxane. Among them, in view of the lubricity (piercing properties), polydimethylsiloxane and polydiethylsiloxane are exemplary, and polydimethylsiloxane is exemplary.

The content of the polydiorganosiloxane (2) is not limited. In view of a better balance of the lubricity, adhesiveness, and film formability, the content of the polydiorganosiloxane (2) based on the total mass of the polyorganosiloxane (1), the polydiorganosiloxane (2), and the amino group-containing polyorganosiloxane (3) or the hydroxy group-containing polyorganosiloxane (4) can be 40 to 75% by mass, for example, 45 to 75% by mass, for example, 45 to 65% by mass, for example, 50 to 65% by mass, for example, 55 to 65% by mass. With an amount in this range, the lubricity (piercing easiness, piercing resistance reduction effect) and durability can be enhanced more effectively. When two or more polydiorganosiloxanes (2) are contained, the content means the total content of the polydiorganosiloxanes (2).

The coating agent can contain the polydiorganosiloxane (2) in such an amount that the ratio by mass to the amino group-containing polyorganosiloxane (3) or the hydroxy group-containing polyorganosiloxane (4) is 0.7 to 3.0. With such an amount, the lubricity (piercing easiness, piercing resistance reduction effect) and durability can be enhanced more effectively. In view of a further effect of enhancing the lubricity and durability, the ratio by mass of the polydiorganosiloxane (2) to the amino group-containing polyorganosiloxane (3) or the hydroxy group-containing polyorganosiloxane (4) can be in a range of 0.9 to 2.5, for example, 1.1 to 2.4, for example, 1.1 to 2.0, for example, 1.5 to 2.0.

The amino group-containing polyorganosiloxane (3) is represented by the following general formula (3).

[Chem. 11]

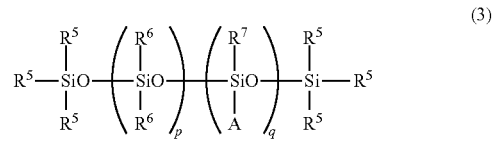

(3)

When two or more structural units of the formula: —Si(R$^6$)$_2$O— are present (p is 2 or more), the structural units may be the same or different. For example, when two or more structural units of the formula: —Si(R$^7$)(A)O— are present (q is 2 or more), the structural units may be the same or different.

When the coating agent contains the amino group-containing polyorganosiloxane (3), the coating agent may contain one amino group-containing polyorganosiloxane (3) alone or may contain two or more amino group-containing polyorganosiloxanes (3).

The amino group-containing polyorganosiloxane (3) can be bonded (adhere) to a base material by interacting with the base material, for example, with a hydroxy group present on a surface of the base material (for example, a hydroxy group on a surface of a metal base material) via an amino group (the substituent "A" in the general formula (3)). Thus, the coating agent containing the amino group-containing polyorganosiloxane (3) can be excellent in the film formability. Furthermore, the polyorganosiloxane (1) and the polydiorganosiloxane (2) can be firmly held in a film formed of the amino group-containing polyorganosiloxane (3). Hence, the coating agent can be also excellent in lubricity (piercing properties) in addition to durability. In addition, the organosiloxane moiety (—Si(R$^6$)$_2$O—) present in the amino group-containing polyorganosiloxane (3) can impart lubricity (piercing easiness). Accordingly, a needle surface-treated with the coating agent can maintain high lubricity, leading to small friction (puncture resistance) in use to make it possible to effective relieve pain experienced by patients.

In the general formula (3), R$^5$ is a monovalent hydrocarbon group or a —OR$^8$ group. For example, plural R$^5$s may be the same or different. The monovalent hydrocarbon group has the same definition as that in the general formula (1), and thus the explanation is omitted here. Among them, from the viewpoint of a further effect of enhancing the lubricity and durability and of the compatibility with solvents, each R$^5$ can be a linear or branched alkyl group having 1 to 16 carbon atoms, for example, a linear or branched alkyl group having 1 to 8 carbon atoms, for example, a linear or branched alkyl group having 1 to 4 carbon atoms, for example, a methyl group.

In addition, regarding —OR$^8$ as R$^5$, each R$^8$ independently represents a substituted or unsubstituted monovalent hydrocarbon group having 1 to 4 carbon atoms. For example, when plural R$^5$s are each a —OR$^8$ group, the plural —OR$^8$ groups may be the same or different to each other. Here, examples of monovalent hydrocarbon groups include, but are not limited to, linear or branched alkyl groups having 1 to 4 carbon atoms (a methyl group, an ethyl group, an n-propyl group, an isopropyl group, an n-butyl group, an isobutyl group, a sec-butyl group, a tert-butyl group), linear or branched alkenyl groups having 2 to 4 carbon atoms (a vinyl group, a 1-propenyl group, a 2-propenyl group (allyl group), an isopropenyl group, a 1-butenyl group, a 2-butenyl group, a 3-butenyl group), cycloalkyl groups having 3 or 4 carbon atoms (a cyclopropyl group, a cyclobutyl group). Among them, from the viewpoint of a further effect of enhancing lubricity and of the adhesiveness to a base material, a methyl group and an ethyl group are exemplary.

In the general formula (3), each R$^6$ and each R$^7$ represents a monovalent hydrocarbon group. For example, R$^6$s in the organosiloxane moiety (—Si(R$^6$)$_2$O—) and R$^7$s in the structural unit of the formula: —Si(R$^7$)(A)O— may be the same or different. The monovalent hydrocarbon group is not limited, and has the same definition as the substituent "R$^5$", that is, the same definition as that in the general formula (1) and thus the explanation is omitted. Among them, from the viewpoint of a further effect of enhancing lubricity and of the availability, each R$^6$ and each R$^7$ can be a linear alkyl group having 1 to 4 carbon atoms, for example, a methyl group.

In the general formula (3), A represents an amino group-containing group. Here, when plural "A"s are present (q is 2 or more), "A"s may be the same or different. Examples of amino group-containing groups include, but are not limited to, a β-aminoethyl group, a γ-aminopropyl group, an N-(β-aminoethyl)aminomethyl group, and a γ-(N-(β-aminoethyl)amino)propyl group. Among them, from the viewpoint of a further effect of enhancing lubricity and of the adhesiveness to a base material, a γ-aminopropyl group, an N-(β-aminoethyl)aminomethyl group, or a γ-(N-(β-aminoethyl)amino)propyl group is exemplary, a γ-(N-(β-aminoethyl)amino)propyl group or a γ-aminopropyl group is exemplary, and a γ-(N-(β-aminoethyl)amino)propyl group is exemplary. That is, in an exemplary embodiment, in the general formula (3), each R$^5$ is independently a linear or branched alkyl group having 1 to 4 carbon atoms, each R$^6$ and each R$^7$ is independently a linear or branched alkyl group having 1 to 4 carbon atoms, and A is a γ-aminopropyl group, a N-(β-aminoethyl)aminomethyl group, or a γ-(N-(β-aminoethyl)amino)propyl group. In addition, in an exemplary embodiment, in the general formula (3), R$^5$ is a methyl group, R$^6$ and R$^7$ are each a methyl group, and A is a γ-(N-(β-aminoethyl)amino)propyl group.

In addition, in the general formula (3), q is an integer in a range of 1 to 100, for example, an integer in a range of 3 to 20, for example, an integer in a range of 3 to 15, for example, an integer in a range of 4 to 10. For example, p is such an integer that satisfies the relationship (ratio by mole) with q, p:q=5:1 to 100:1. For example, p:q=10:1 to 100:1, for example, 20:1 to 80:1, for example, 30:1 to 50:1. With such p and q, a sufficient number of amino groups can be present in the amino group-containing polyorganosiloxane (3), and thus sufficient adhesiveness to a base material can be achieved. In addition, with such p and q, a sufficient number of organosiloxane moieties can be present in the amino group-containing polyorganosiloxane (3), and thus the coating agent can exhibit more sufficient lubricity to further reduce the friction (puncture resistance) on a base material. While p is not limited as long as the above relationship is satisfied, p can be an integer in a range of 10 to 800, for example, 60 to 400, for example, 100 to 300.

The molecular weight of the amino group-containing polyorganosiloxane (3) is not limited. The weight average molecular weight can be in a range of 5,000 to 50,000, for example, 7,500 to 30,000, for example, 10,000 to 20,000.

The method for producing the amino group-containing polyorganosiloxane (3) is not limited. For example, the amino group-containing polyorganosiloxane (3) can be produced using any suitable known technique, or by appropriately modifying a known technique.

The content of the amino group-containing polyorganosiloxane (3) is not limited. In view of a better balance of the lubricity, adhesiveness, and film formability, the content of the amino group-containing polyorganosiloxane (3) based on the total mass of the polyorganosiloxane (1), the polydiorganosiloxane (2), and the amino group-containing polyorganosiloxane (3) can be 24 to 57% by mass, for example, 24 to 54% by mass, for example, 32 to 54% by mass, for example, 32 to 45% by mass, for example, 32 to 41% by mass. With such an amount, the adhesiveness to a base material and the lubricity (piercing easiness, piercing resistance reduction effect) can be enhanced more effectively. In addition to that, the safety of a coating agent can be further enhanced, which is exemplary in use for a medical application, such as a needle. When two or more amino group-containing polyorganosiloxanes (3) are contained, the content means the total content of the amino group-containing polyorganosiloxanes (3).

[Hydroxy group-containing polyorganosiloxane (4)]

The hydroxy group-containing polyorganosiloxane (4) is represented by the following general formula (4).

[Chem. 12]

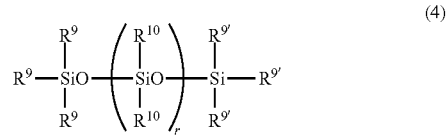

(4)

When two or more structural units of the formula: —Si(R$^{10}$)$_2$O— are present (r is 2 or more), the structural units may be the same or different.

When the coating agent contains the hydroxy group-containing polyorganosiloxane (4), the coating agent may contain one hydroxy group-containing polyorganosiloxane (4) alone or two or more hydroxy group-containing polyorganosiloxanes (4).

In the hydroxy group-containing polyorganosiloxane (4), hydroxy groups at both the ends can be bonded to a base material to form a film. Thus, the coating agent containing the hydroxy group-containing polyorganosiloxane (4) can be excellent in the film formability. In addition, the hydroxy group-containing polyorganosiloxane (4) can have hydroxy groups (R$^9$ and R$^{9'}$) at both the ends. Since the hydroxy groups interact with a base material, for example, hydroxy groups on a base material, the coating agent can be excellent in the adhesiveness to a base material. Furthermore, the polyorganosiloxane (1) and the polydiorganosiloxane (2) can be firmly held in a film formed of the hydroxy group-containing polyorganosiloxane (4). Hence, the coating agent can be also excellent in durability. Accordingly, when a needle surface-treated with the coating agent is used, the separation of a film (coating agent) from a needle surface can be suppressed even in multiple punctures into a rubber cap. Accordingly, in a needle surface-treated with the coating agent, the separation of a film (coating agent) from a needle surface can be suppressed even in multiple punctures into a rubber cap.

In the general formula (4), each $R^9$ and each $R^{9'}$ represents a monovalent hydrocarbon group or a hydroxy group (—OH). For example, $R^9$ and $R^{9'}$ may be the same or different. For example, plural $R^9$'s in —Si$(R^9)_3$ may be the same or different. For example, plural $R^{9'}$'s in —Si$(R^{9'})_3$ may be the same or different. However, at least one of $R^9$'s is a hydroxy group (—OH) and at least one of $R^{9'}$'s is a hydroxy group (—OH). In view of a further effect of enhancing the film formability, one or two of $R^9$'s and/or one or two of $R^{9'}$'s are preferably a hydroxy group, for example, one of $R^9$'s is a hydroxy group and one of $R^{9'}$'s is a hydroxy group.

The monovalent hydrocarbon groups as $R^9$'s and $R^{9'}$'s have the same definition as that in the general formula (1) and thus the explanation is omitted. Among them, from the viewpoint of a further effect of enhancing lubricity, the monovalent hydrocarbon groups as $R^9$'s and $R^{9'}$'s each can be a linear or branched alkyl group having 1 to 16 carbon atoms, for example, a linear or branched alkyl group having 1 to 8 carbon atoms, for example, a linear or branched alkyl group having 1 to 4 carbon atoms, for example, a methyl group.

In the general formula (4), $R^{10}$ represents a monovalent hydrocarbon group. For example, $R^{10}$s present in one structural unit may be the same or different. The monovalent hydrocarbon groups as $R^{10}$'s have the same definition as that in $R^9$'s and $R^{9'}$'s and thus the explanation is omitted. From the viewpoint of a further effect of enhancing lubricity and durability and of the compatibility with solvents, each $R^{10}$ can be a linear or branched alkyl group having 1 to 16 carbon atoms, for example, a linear or branched alkyl group having 1 to 8 carbon atoms, for example, a linear or branched alkyl group having 1 to 4 carbon atoms, for example, a methyl group.

In an exemplary embodiment, in the general formula (4), one of $R^9$'s and $R^{9'}$'s is a hydroxy group, the other $R^9$'s and $R^{9'}$'s are each independently a linear or branched alkyl group having 1 to 4 carbon atoms, and each $R^{10}$ is independently a linear or branched alkyl group having 1 to 4 carbon atoms. In addition, in an exemplary embodiment, in the general formula (4), one of $R^9$'s and $R^{9'}$'s is a hydroxy group, the other $R^9$'s and $R^{9'}$'s are each a methyl group, and $R^{10}$'s are each a methyl group.

In addition, r is an integer in a range of 1,000 to 30,000, for example, an integer in a range of 5,000 to 20,000, for example, an integer in a range of 10,000 to 15,000. With r in the above range, the hydroxy group-containing polyorganosiloxane (4) can exhibit sufficient film formability. The molecular weight of the hydroxy group-containing polyorganosiloxane (4) is not limited, but the weight average molecular weight can be 10,000 to 2,000,000, for example, 100,000 to 1,050,000, for example, 100,000 to 1,000,000, for example, 500,000 to 1,000,000.

The content of the hydroxy group-containing polyorganosiloxane (4) is not limited. In view of a better balance of the lubricity, adhesiveness, and film formability, the content based on the total mass of the polyorganosiloxane (1), the polydiorganosiloxane (2), and the hydroxy group-containing polyorganosiloxane (4) can be 2.4 to 5.5% by mass, for example, 2.9 to 5.5% by mass, for example, 3.2 to 5.5% by mass, for example, 3.2 to 4.6% by mass, for example, 3.2 to 3.9% by mass. When two or more hydroxy group-containing polyorganosiloxanes (4) are contained, the content means the total content of the hydroxy group-containing polyorganosiloxanes (4).

[Other components]

For example, the coating agent contains the polyorganosiloxane (1), the polydiorganosiloxane (2), and the amino group-containing polyorganosiloxane (3) or the hydroxy group-containing polyorganosiloxane (4). The coating agent may be constituted only of the polyorganosiloxane (1) to (3), or only of (1), (2), and (4), or may contain other components in addition to the above components. For example, usable other components are not limited, and examples include components that are commonly added to coating agents, for example, a coating agent for coating a medical instrument (for example, injection needle, catheter, cannula). Examples include a condensation reaction catalyst, an antioxidant, a pigment, a surfactant, a slipping agent, and an undercoating agent. The content of the other components is not limited unless, for example, the effects obtained by the polyorganosiloxanes (1) to (3) are impaired. For example, the content based on the total amount of the polyorganosiloxanes (1) to (3) or on the total amount of the polyorganosiloxanes (1), (2), and (4) can be about 0.1 to 5% by mass.

In addition, the coating agent may contain an organic solvent. The organic solvent is not limited, and the same solvents as used in coating agents can be used. Examples include: fluorocarbon solvents, such as 1,1,2-trichloro-1,2,2-trifluoroethane; chlorine-containing hydrocarbons, such as methylene chloride (dichloromethane) and chloroform; aliphatic hydrocarbons, such as butane, pentane, and hexane; aromatic hydrocarbons, such as benzene, toluene, and xylene; esters, such as ethyl acetate and butyl acetate; water insoluble ketones, such as methyl isobutyl ketone; ethers, such as tetrahydrofuran (THF), butyl ether, and dioxane; aliphatic alcohols, such as methanol, ethanol, and isopropanol; volatile siloxanes, such as hexamethyldisiloxane and octamethylcyclotetrasiloxane; and acetonitrile, dimethylformamide (DMF), dimethylsulfoxide (DMSO), and carbon disulfide. These organic solvents may be used alone or as a mixed solvent in combination of two or more thereof. The amount of the organic solvent used is not limited. In view of the easiness of coating or the like, the total concentration of the polyorganosiloxanes (1) to (3) or the total concentration of the polyorganosiloxanes (1), (2), and (4) can be 5 to 80% by mass, for example, about 50 to 75% by mass. For example, when a medical instrument (for example, needle) is coated with the coating agent, the coating agent may be further diluted with the organic solvent mentioned above. In this case, the coating agent can be diluted with the organic solvent so that the total concentration of the polyorganosiloxanes (1) to (3) or the total concentration of the polyorganosiloxanes (1), (2), and (4) is 1 to 10% by mass, for example, 3 to 7% by mass.

The method for producing the coating agent is not limited, and a method may be used in which the polyorganosiloxanes (1) to (3) or the polyorganosiloxanes (1), (2), and (4), and, if desired, the aforementioned other components are stirred and mixed. In this method, an organic solvent can be added. This can enable easy coating of a medical instrument (for example, needle) or the like in practice. The organic solvent is not limited, and the organic solvents as described above in other components can be used. The condition in stirring and mixing is not limited. For example, the temperature for stirring and mixing can be 25 to 130° C., for example, 40 to 100° C. In addition, the time for stirring and mixing can be 0.5 to 8 hours, for example, 1 to 6 hours. At such conditions, the polyorganosiloxanes (1) to (3) or the polyorganosiloxane (1), (2), and (4), and as desired, the other components can be uniformly mixed without undesired reaction, for example.

[Exemplary composition]

From the viewpoint of further enhancing lubricity (piercing properties) while obtaining a film excellent in durability, the polyorganosiloxane component contained in the coating agent according can be constituted only of the polyorganosiloxanes (1) to (3) or only of the polyorganosiloxanes (1), (2), and (4), and for example is constituted only of the polyorganosiloxanes (1) to (3).

Furthermore, an exemplary coating agent can contain: 2.0 to 6.0% by mass of the polyorganosiloxane (1); 40 to 75% by mass of the polyorganosiloxane (2); and 24 to 57% by mass of the amino group-containing polyorganosiloxane (3). For example, the coating agent can contain: 2.4 to 5.5% by mass of the polyorganosiloxane (1); 45 to 75% by mass of the polyorganosiloxane (2); and 24 to 54% by mass of the amino group-containing polyorganosiloxane (3). For example, the coating agent can contain: 3.0 to 4.5% by mass of the polyorganosiloxane (1); 45 to 65% by mass of the polyorganosiloxane (2); and 32 to 54% by mass of the amino group-containing polyorganosiloxane (3). For example, the coating agent can contain: 3.2 to 4.1% by mass of the polyorganosiloxane (1); 55 to 65% by mass of the polyorganosiloxane (2); and 32 to 41% by mass of the amino group-containing polyorganosiloxane (3) (for example, provided that, in the above, the total amount of the polyorganosiloxanes (1) to (3) is 100% by mass). With such a blending ratio, a film having lubricity (piercing properties) and durability enhanced in a balanced manner can be formed.

[Use of coating agent]

The coating agent can enhance lubricity and durability of a subject to be coated. Thus, the coating agent can be suitably used in the field of medical instruments (for example, needle, catheter, cannula) where such features are desired. Accordingly, the present disclosure also provides a medical instrument surface-treated by a curing treatment of the coating agent. In addition, the present disclosure also provides a method for producing a medical instrument, the method including subjecting a surface of a medical instrument to a curing treatment with the coating agent.

The medical instrument may be used in any suitable purpose. For example, examples include a catheter, a cannula, a needle, a three-way stopcock, and a guidewire. Among them, the coating agent can be used in a catheter, a cannula, a needle, or a three-way stopcock, for example, in a needle, for example, in a medical needle (for example, injection needle). That is, in an exemplary embodiment, a needle obtained through a surface treatment by a curing treatment of the coating agent is provided.

According to the coating agent, the friction at the initial puncture is reduced. For example, in a needle, for example, a medical needle (for example, injection needle), a smaller initial (zero-puncture) puncture resistance (maximum resistance value) is exemplary. Specifically, the puncture resistance (maximum resistance value) can be less than 55 mN, for example, 45 mN or less. For example, the lower limit of the initial (zero-puncture) puncture resistance (maximum resistance value) is 0 mN since a smaller value is exemplary, but the lower limit is not limited, and generally a resistance of 10 mN or more can be acceptable. The puncture resistance (maximum resistance value) is measured by a method described in Examples.

In an exemplary coating agent, in addition to the reduced friction at puncture, excellent durability of the coating can be achieved. Therefore, from the viewpoint of these features, in a needle, for example, medical needle (for example, injection needle), a smaller puncture resistance (maximum resistance value) after puncturing a rubber sheet 10 times with the needle is exemplary.

Specifically, the puncture resistance (maximum resistance value) can be less than 130 mN, for example, 105 mN or less, for example, 100 mN or less. For example, the lower limit of puncture resistance (maximum resistance value) after piecing a rubber sheet 10 times with the needle can be 0 mN since a smaller value is exemplary, but the lower limit is not limited, and a value of 10 mN or more can be acceptable. The puncture resistance (maximum resistance value) is measured by a method described in Examples.

In addition, the present disclosure also provides a method for producing a needle (medical needle), the method including subjecting a surface of a needle (medical needle) to a curing treatment with the coating agent.

The medical instrument (as a base material) may be formed of any material and the same materials as conventional materials can be used. Although an embodiment where the medical instrument is a needle will be described below as one example, the present disclosure is not limited to this embodiment. Aspects of the present disclosure can be applied to any desired medical instrument, for example, by using a material for forming the medical instrument instead of a material for forming a needle.

The needle may be formed of any material, and the same materials as commonly used in needles, for example, medical needles (for example, injection needles), such as metal materials and polymer materials, can be used. Examples of metal materials include, but not limited to, various stainless steels (SUS), such as SUS304, SUS316L, SUS420J2, and SUS630, gold, platinum, silver, copper, nickel, cobalt, titanium, iron, aluminum, tin, and various alloys, such as a nickel-titanium (Ni—Ti) alloy, a nickel-cobalt (Ni—Co) alloy, a cobalt-chromium (Co—Cr)alloy, and a zinc-tungsten (Zn—W) alloy, as well as a metal-ceramic composite. The metal materials may be used alone or in combination of two or more thereof. Hydroxy groups on a surface of the metal materials can be bonded to the amino groups of the amino group-containing polyorganosiloxane (3) and the hydroxy groups of the polyorganosiloxane (1) having a hydroxy group at an end and the hydroxy group-containing polyorganosiloxane (4) which constitute the coating agent. Thus, a needle formed of the above materials can be excellent in the adhesiveness to a film of the coating agent. Examples of the polymer materials include, but not limited to: polyamide resins, such as nylon 6, nylon 11, nylon 12, and nylon 66 (all registered name); polyolefin resins, such as polyethylene resins, for example, linear low density polyethylene (LLDPE), low density polyethylene (LDPE), and high density polyethylene (HDPE), and a polypropylene resin; modified polyolefin resins; epoxy resins; urethane resins; diallylphthalate resins (allyl resins); polycarbonate resins; fluoro resins; amino resins (urea resins, melamine resins, benzoguanamine resins); polyester resins; styrol resins; acrylic resins; polyacetal resins; vinyl acetate resins; phenol resins; vinyl chloride resins; silicone resins (silicon resins); polyether resins; and polyimide resins. The polymer materials may be used alone or in combination of two or more thereof.

In addition, from the viewpoint of tendency to interact with functional groups, such as an amino group and a hydroxy group, of the coating agent, a base material surface-treated with the coating agent can be a base material having a functional group, such as a hydroxy group, a carboxyl group, or amino. For example, when the base material is a metal material, the surface of the metal material is coated with an oxidized film to thus have a hydroxy group or the like, and therefore has high adhesiveness to the coating agent, which is exemplary. In addition, in the case of a base material that less interacts with a functional group, such as an amino group or a hydroxy group, of the coating agent, a functional group, such as a hydroxy group, can be added to the base material by a plasma treatment or the like to thereby enhance the adhesiveness of the coating agent to the base material.

The method of the surface treatment with the coating agent is not limited, and a coating film containing the coating agent can be subjected to a curing treatment by heating or radiation. For example, the present disclosure also provides a method for producing a medical instrument (for example, a needle), the method including forming a coating film containing the coating agent on a surface of a medical instrument (for example, a needle), heating or irradiating the coating film to perform a curing treatment. Alternatively, for example, in the method of surface-treatment with the coating agent, a curing treatment can be performed by heating and moisturizing a coating film containing the coating agent. For example, the present disclosure also provides a method for producing a medical instrument (for example, a needle), the method including forming a coating film containing the coating agent on a surface of a medical instrument (for example, a needle), and heating and moisturizing the coating film to perform a curing treatment.

The method of forming a coating film containing a coating agent is not limited, and any suitable coating method can be applied. For example, as a technique for coating, a dipping method, an application and printing method, a spraying method, blush application, a spin coating method, or a coating agent impregnation sponge coating method may be applied. For example, when a coating agent is applied on a needle surface, the coating agent may be prevented from entering the inside of the needle by feeding air or the like inside the needle. For example, this can prevent the clogging of the needle with the coating agent. In addition, a solvent may be vaporized from the coating agent applied on a base material by natural drying, air drying, or heating, as needed, and in some cases, the coating agent may be procured at the same time.

For example, when it is desired to form a coating film on only a part of a needle surface, only the part of the needle surface intended to receive the coating film is dipped in a coating agent to apply the coating agent (coating solution) on the part of the needle surface. For example, this can result in forming a coating film on a desired surface portion of the needle surface. For example, if it is difficult to dip only a part of the needle surface in the coating agent, the needle surface portion where a coating film does not have to be formed can be protected (coated) with an appropriate removable (detachable) member or material prior to dipping, and the needle is then dipped in the coating agent to apply the coating agent on the needle surface. Thereafter, for example, the protection member (material) on the needle surface portion where a coating film does not have to be formed is removed, thereby forming a coating film on a desired surface portion of the needle surface. However, in the present disclosure, the forming method is not limited at all, and any suitable method can be appropriately used to form a coating film. For example, if it is difficult to dip only a part of a needle surface in a coating agent, instead of a dipping method, any other coating technique (for example, an application method or a spraying method) may be adopted. For example, when both of the outer surface and the inner surface of the needle surface have to have the lubricity or durability, a dipping method can be used in that both the outer and inner surfaces can be coated at once.

For example, after forming a coating film containing the coating agent, the coating film can be subjected to a curing treatment. In the curing treatment (surface treatment), the method of the curing treatment (surface treatment) in the case where a coating film containing the coating agent is heated is not limited. Examples of curing treatments (surface treatments) include a heat treatment under a normal pressure (the atmosphere), a heat treatment under pressured vapor, and a heat treatment using ethylene oxide gas (EOG).

For example, in the case of a heat treatment under a normal pressure (the atmosphere), the heat treatment conditions (reaction conditions) are not limited as long as the desired effect (for example, lubricity, durability) can be achieved. The heating temperature can be in a range of 50 to 150° C., for example, 60 to 130° C. In addition, the heating time can be in a range of 2 to 48 hours, for example, 15 to 30 hours. Under such reaction conditions, the amino group-containing polyorganosiloxane (3) (amino group) or the polyorganosiloxane (1) containing a hydroxy group at an end, and the hydroxy group-containing polyorganosiloxane (4) (hydroxy group) can be strongly bonded to a base material. In addition, the polyorganosiloxane (1) containing a hydroxy group at an end and the hydroxy group-containing polyorganosiloxane (4) (hydroxy group) can react with a base material surface to form a strong film. In addition, as a heating means (device), for example, an oven, a dryer, a microwave heater, or the like can be used.

For example, the conditions of a heat treatment (reaction conditions) in the case of a heat treatment under a pressured vapor are also not limited as long as the desired effect (for example, lubricity, durability) can be achieved. The heating temperature can be in a range of 100 to 135° C., for example, 105 to 130° C. In addition, the heating time can be in a range of 1 to 120 minutes, for example, 10 to 60 minutes. Furthermore, the pressure may be appropriately selected in view of the desired reactivity (for example, lubricity, durability, bonding with a base material). Under such reaction conditions, the amino group-containing polyorganosiloxane (3) (amino group), the polyorganosiloxane (1) containing a hydroxy group at an end, and the hydroxy group-containing polyorganosiloxane (4) (hydroxy group) can be strongly bonded to the base material. In addition, the polyorganosiloxane (1) containing a hydroxy group at an end and the hydroxy group-containing polyorganosiloxane (4) (hydroxy group) can react with a base material surface to form a strong film. In addition, under the above conditions, a needle can be sterilized at the same time. In addition, as a heating means (device), for example, a Koch's sterilizer, an autoclave, or the like can be used.

For example, the heat treatment conditions (reaction conditions) in the case of the heat treatment using ethylene oxide gas (EOG) is also not limited as long as the desired effect (for example, lubricity, durability) can be achieved. The heating temperature can be 40 to 135° C., for example, 45 to 80° C. In addition, the heating time can be 1 to 300 minutes, for example, 20 to 250 minutes. Furthermore, the pressure may be appropriately selected in view of the desired reactivity (for example, lubricity, durability, bonding with a base material). Under such reaction conditions, the amino group-containing polyorganosiloxane (3) (amino group), the polyorganosiloxane (1) containing a hydroxy group at an end, and the hydroxy group-containing polyorganosiloxane (4) (hydroxy group) can be strongly bonded to a base material. In addition, the polyorganosiloxane (1) containing a hydroxy group at an end and the hydroxy group-containing polyorganosiloxane (4) (hydroxy group) can react with a base material surface to form a strong film. In addition, under the above conditions, a needle can be sterilized at the same time.

For example, the radiation in the case of the surface treatment (curing treatment) by irradiation is not limited. The radiation may be gamma rays (γ-rays), electron rays, neutron rays, or X-rays. Among them, gamma rays or electron rays are exemplary. For example, the irradiation not only facilitates the curing treatment of the coating agent but also sterilize a needle. The irradiation conditions (reaction conditions) are not limited as long as the desired effect (for example, lubricity, durability) can be achieved. For example, in the case of irradiation with gamma rays, the conditions, such as dose and irradiation time, are not limited, but generally, the dose of γ-rays can be in a range of 10 to 50 kGy, for example, 15 to 25 kGy. Under such irradiation conditions, the amino group-containing polyorganosiloxane (3) (amino group), the polyorganosiloxane (1) containing a hydroxy group at an end, and the hydroxy group-containing polyorganosiloxane (4) (hydroxy group) can be strongly bonded to a base material. In addition, the polyorganosiloxane (1) containing a hydroxy group at an end and the hydroxy group-containing polyorganosiloxane (4) (hydroxy group) can react with a base material surface to from a strong film.

EXAMPLES

Exemplary effects of the present disclosure will be described with reference to the following Examples and Comparative Examples. However, the technical scope of the present disclosure is not to be limited only to the following Examples. Unless otherwise specified, the operations in Examples were carried out at a room temperature (25° C.). In addition, unless otherwise specified, "%" and "parts" means "% by mass" and "parts by mass", respectively.

Synthetic Example 1

Synthesis of Both-End Amino Group-Containing Polyorganosiloxane (5)

A both-end amino group-containing polyorganosiloxane (5) having the following structure was synthesized in the same manner as in Preparation Example 1 of JP-A-7-178159 as follows.

[Chem. 13]

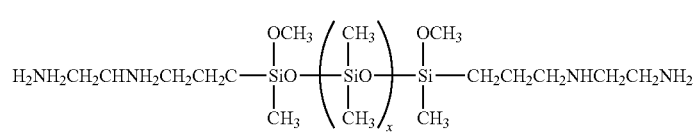

Both-end amino group-containing polyorganosiloxane x = 12000 in the structure

That is, to 100 parts by mass of a both-end silanol group-containing polydimethylsiloxane of the following structure (weight average molecular weight=about 900,000), 390 parts by mass of toluene was added, the mixture was stirred at 50° C. for 3 hours, and then 20 parts by mass of γ-[N-(β-aminoethyl)amino]propylmethyldimethoxysilane was added thereto, followed by reaction at 80° C. for 12 hours, thereby obtaining a both-end amino group-containing polyorganosiloxane (5) (weight average molecular weight=about 900,000).

[Chem. 14]

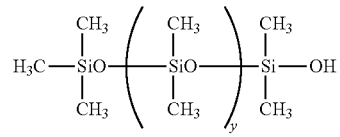

Both-end silanol group-containing polydimethylsiloxane

Comparative Example 1

120 parts by mass of the both-end amino group-containing polyorganosiloxane (5) synthesized in Synthetic Example 1, 730 parts by mass of a polydimethylsiloxane (2) of the following structure (weight average molecular weight=about 3000, n=38 in the general formula (2)), 660 parts by mass of an amino group-containing polyorganosiloxane (3) of the following structure (weight average molecular weight=about 15,000), 1700 parts by mass of toluene, and 200 parts by mass of ethanol were added, and the mixture was stirred at 85° C. for 2 hour to obtain a comparative coating agent 1.

[Chem. 15]

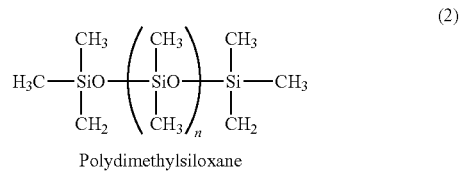

Polydimethylsiloxane (2)

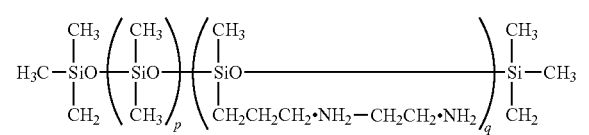

Amino group-containing polyorganosiloxane wherein p = 5, p:q (by mole) = 40:1

(3)

(5)

Comparative Example 2

10 parts by mass of the polydimethylsiloxane (2) of the above structure (weight average molecular weight=about 3000, n=38 in the general formula (2)) used in Comparative Example 1, 15 parts by mass of the amino group-containing polyorganosiloxane (3) of the above structure (weight average molecular weight=about 15000), 70 parts by mass of toluene, and 5 parts by mass of ethanol were added and the mixture was stirred at 40° C. for 2 hours to obtain a comparative coating agent 2.

Example 1

A polydimethylsiloxane (1) of the following structure (weight average molecular weight=about 592,000, m=8,000 in the general formula (1)), a polydimethylsiloxane (2) of the following structure (weight average molecular weight=about 3,000, n=38 in the general formula (2)), an amino group-containing polyorganosiloxane (3) of the following structure (weight average molecular weight=about 15,000), toluene, and ethanol were added so as to give a composition as shown in Table 1 below, and the mixture was stirred and mixed at 45° C. for 4 hours to obtain a coating agent 1 (Example 1). In Table 1 below, the polydimethylsiloxane (1) is referred to as "compound 1", the polydimethylsiloxane (2) is as "compound 2", and the amino group-containing polyorganosiloxane (3) is as "compound 3".

[Chem. 16]

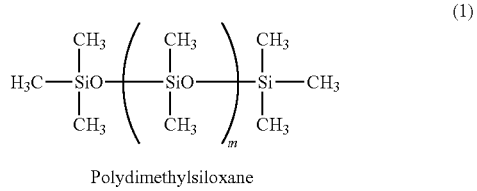

Polydimethylsiloxane (1)

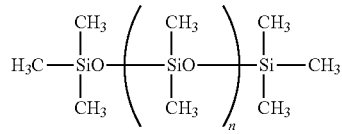

Polydimethylsiloxane (2)

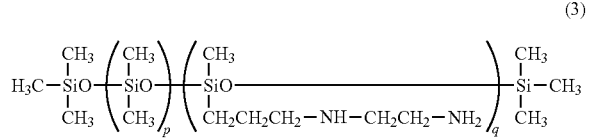

Amino group-containing polyorganosiloxane (3)

wherein, p = 5, P:q (by mole) = 40:1

Example 2

A coating agent 2 was obtained in the same manner as in Example 1 except that the polydimethylsiloxane (1) (weight average molecular weight=about 592,000, m=8,000 in the general formula (1)) in Example 1 was changed to a polydimethylsiloxane (1) having a weight average molecular weight=about 444,000 (m=6,000 in the general formula (1)).

Example 3

A coating agent 3 was obtained in the same manner as in Example 1 except that the polydimethylsiloxane (1) (weight average molecular weight=about 592,000, m=8,000 in the general formula (1)) in Example 1 was changed to a polydimethylsiloxane (1) with a weight average molecular weight=about 296,000 (m=4,000 in the general formula (1)).

Examples 4 to 7

Coating agents 4 to 7 were obtained in the same manner as in Example 2 except that the amounts of the compounds 1 to 3 added in Example 2 are changed so as to give the composition as shown in Table 1 below.

TABLE 1

|  |  | Example 1 | Example 2 | Example 3 | Example 4 | Example 5 | Example 6 | Example 7 |
|---|---|---|---|---|---|---|---|---|
| Blending ratio | Compound 1 | 100 | 100 | 100 | 100 | 100 | 100 | 100 |
|  | Compound 2 | 1750 | 1750 | 1750 | 3000 | 2000 | 1350 | 730 |
|  | Compound 3 | 990 | 990 | 990 | 990 | 990 | 990 | 990 |
|  | Toluene | 1200 | 1200 | 1200 | 1600 | 1200 | 1200 | 1200 |
|  | Ethanol | 100 | 100 | 100 | 100 | 100 | 100 | 100 |
| Percentage of silicone component | Compound 1 | 3.5% | 3.5% | 3.5% | 2.4% | 3.2% | 4.1% | 5.5% |
|  | Compound 2 | 61.6% | 61.6% | 61.6% | 73.3% | 64.7% | 55.3% | 40.1% |
|  | Compound 3 | 34.9% | 34.9% | 34.9% | 24.2% | 32.0% | 40.6% | 54.4% |
| Mixing ratio (by mass) | Compound 1/compound 2 | 0.06 | 0.06 | 0.06 | 0.03 | 0.05 | 0.07 | 0.14 |
|  | Compound 2/compound 3 | 1.8 | 1.8 | 1.8 | 3.0 | 2.0 | 1.4 | 0.7 |
| Polymerization degree | Polymerization degree of compound 1 (m) | 8000 | 6000 | 4000 | 6000 | 6000 | 6000 | 6000 |
|  | Polymerization degree of compound 2 (n) | 38 | 38 | 38 | 38 | 38 | 38 | 38 |
|  | m/n | 211 | 158 | 105 | 158 | 158 | 158 | 158 |

[Evaluation: measurement of piercing resistance (puncture resistance)]

For the coating agents 1 to 7 obtained in Examples 1 to 7 and the comparative coating agents 1 to 2 obtained in Comparative Examples 1 to 2, the piercing resistance was measured according to the following method.

(Coating of injection needle 1: heating)

Dichloromethane was added to each coating agent to dilute the coating agent so that the silicone component concentration was about 5% by mass, thereby obtaining a clear, colorless coating liquid. The silicone component concentration in Examples 1 to 7 refers to the total concentration of the polydimethylsiloxane (1), the polydimethylsiloxane (2), and the amino group-containing polyorganosiloxane (3) in the coating liquid. In addition, in Comparative Example 1, the silicone component concentration refers to the total concentration of the both-end amino group-containing polyorganosiloxane (5), the polydimethylsiloxane (2), and the amino group-containing polyorganosiloxane (3) in the coating liquid. Furthermore, in Comparative Example 2, the silicone component concentration refers to the total concentration of the polydimethylsiloxane (2) and the amino group-containing polyorganosiloxane (3) in the coating liquid.

An 18G injection needle (the needle part was made of SUS304) was dipped in each of the coating liquids prepared as described above and was pulled up at a rate of 1000 mm/min using a tensile tester (Autograph AG-1kNIS manufactured by Shimadzu Corporation). The needle was naturally dried at a room temperature for 2 hours. Furthermore, the injection needle was heated in an oven at 105° C. for 24 hours to perform a curing treatment. Injection needles on a surface of which a film was formed with the coating agents 1 to 7 were referred to as injection needles 1 to 7, respectively, and injection needles on a surface of which a film was formed with the comparative coating agents 1 to 2 were referred to as comparative injection needles 1 to 2, respectively.

(Coating of injection needle 2: EOG)

A coating liquid was prepared in the same manner as the above (Coating of injection needle 1: heating).

An 18G injection needle (the needle part was made of SUS304) was dipped in each of the coating liquids prepared as described above and was pulled up at a rate of 1000 mm/min using a tensile tester (Autograph AG-1kNIS manufactured by Shimadzu Corporation). The needle was naturally dried at a room temperature for 2 hours. Furthermore, the injection needle was subjected to a curing treatment using ethylene oxide gas (EOG) at 50° C. for 210 minutes. EOG (ethylene oxide gas) sterilization was applied to the injection needle by the above treatment. In addition, injection needles on a surface of which a film was formed with the coating agents 1 to 7 were referred to as injection needles 8 to 14, respectively, and injection needles on a surface of which a film was formed with the comparative coating agents 1 to 2 were referred to as comparative injection needles 3 to 4, respectively.

(Coating of injection needle 3: high pressure vapor)

A coating liquid was prepared in the same manner as the above (Coating of injection needle 1: heating).

An 18G injection needle (the needle part was made of SUS304) was dipped in each of the coating liquids prepared as described above and was pulled up at a rate of 1000 mm/min using a tensile tester (Autograph AG-1kNIS manufactured by Shimadzu Corporation). The needle was naturally dried at a room temperature for 2 hours. Furthermore, the injection needle was subjected to a curing treatment under high pressure vapor at 121° C. for 20 minutes. High pressure vapor (autoclave) sterilization was applied to the injection needle by the above treatment. In addition, injection needles on a surface of which a film was formed with the coating agents 1 to 7 were referred to as injection needles 15 to 21, respectively, and injection needles on a surface of which a film was formed with the comparative coating agents 1 to 2 were referred to as comparative injection needles 5 to 6, respectively.

(Coating of Injection Needle 4: Radiation)

A coating liquid was prepared in the same manner as the above (Coating of injection needle 1: heating).

An 18G injection needle (the needle part was made of SUS304) was dipped in each of the coating liquids prepared as described above and was pulled up at a rate of 1000 mm/min using a tensile tester (Autograph AG-1kNIS manufactured by Shimadzu Corporation). The needle was naturally dried at a room temperature for 2 hours. Furthermore, the injection needle was irradiated with γ-rays at 20 kGy to perform a curing treatment. Radiation sterilization was applied to the injection needle by the above treatment. In addition, injection needles on a surface of which a film was formed with the coating agents 1 to 7 were referred to as injection needles 22 to 28, respectively, and injection needles on a surface of which a film was formed with the comparative coating agents 1 to 2 were referred to as comparative injection needles 7 to 8, respectively.

(Measurement of Piercing Resistance)

For the injection needles 1 to 28 and comparative injection needles 1 to 8, the sliding resistance value (piercing resistance value) (mN) when a 0.5-mm thickness silicone rubber sheet (Durometer hardness A50) was punctured at an angle of 90 degree and at a rate of 100 mm/min was measured using a tensile tester (Autograph AG-1kNIS manufactured by Shimadzu Corporation). Specifically, the sliding resistance value based on a moving distance of an injection needle was acquired as time-series data. In addition, from the measurement value, the maximum resistance value (mN) was calculated. The measurement was performed after each of the injection needles 1 to 28 and comparative injection needles 1 to 8 punctured a rubber cap 0 time (initial) or 10 times.

Figure 1B:
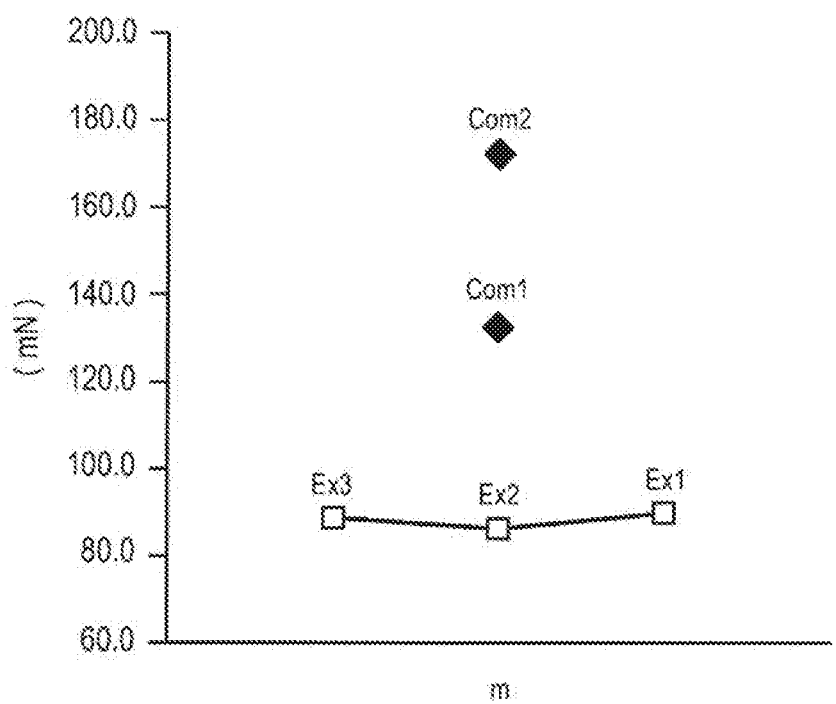
FIG. 1B is a graph showing puncture resistances (sliding resistance values (mN)) after ten punctures of needles surface-treated by heating with coating agents of Examples 1 to 3 (Ex. 1 to 3) and Comparative Examples 1 to 2 (Com. 1 to 2), according to exemplary embodiments.
Figure 2A:
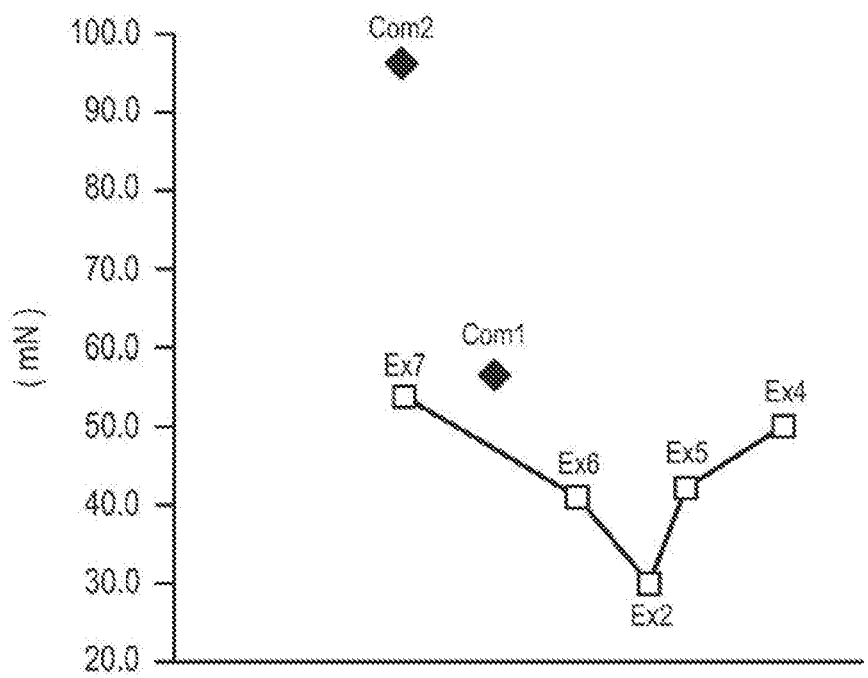
FIG. 2A is a graph showing initial (zero-puncture) puncture resistances (sliding resistance values (mN)) of needles surface-treated by heating with coating agents of Examples 2 and 4 to 7 (Ex. 2, 4 to 7) and Comparative Examples 1 to 2 (Com. 1 to 2), according to exemplary embodiments.
Figure 2B:
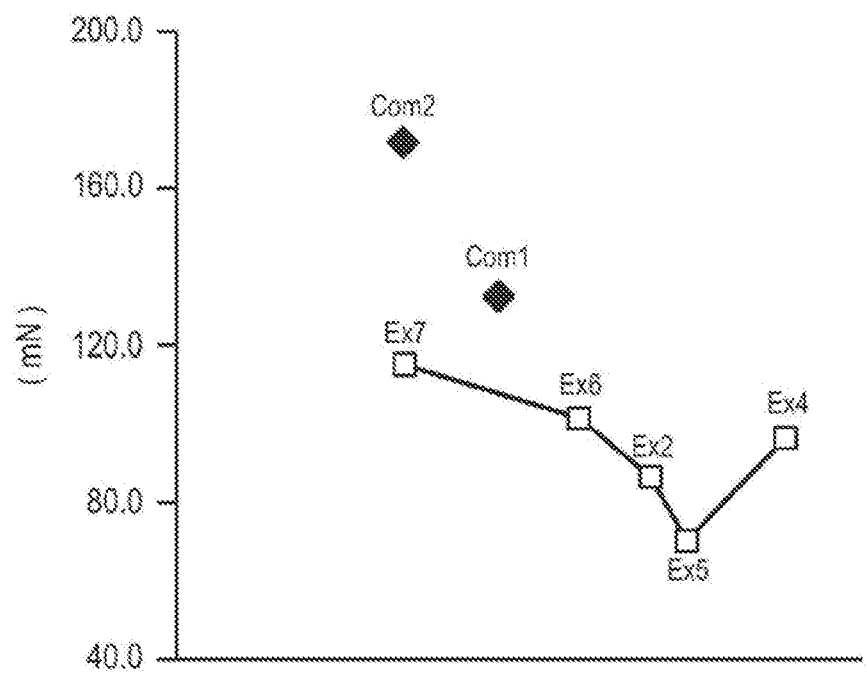
FIG. 2B is a graph showing puncture resistances (sliding resistance values (mN)) after ten punctures of needles surface-treated by heating with coating agents of Example 2 and 4 to 7 (Ex. 2, 4 to 7) and Comparative Examples 1 to 2 (Com. 1 to 2), according to exemplary embodiments.

The results were shown in FIG. 1 and FIG. 2. Specifically, the results of the sliding resistance values (piercing resistance values) (mN) after zero and ten punctures by the injection needles 1 to 3 and comparative injection needles 1 to 2 (coating 1: heating at 105° C. for 24 hours) are shown in FIG. 1A and FIG. 1B, respectively. In addition, the results of the sliding resistance values (piercing resistance values) (mN) after zero and ten punctures by the injection needles 2, 4 to 7 and comparative injection needles 1 to 2 (coating 1: heating at 105° C. for 24 hours) are shown in FIG. 2A and FIG. 2B, respectively.

FIG. 1 is a graph for evaluating dependency of the weight average molecular weight (polymerization degree m) of the compound 1 on the sliding resistance, and FIG. 2 is a graph for evaluating the dependency of the composition (contents) of the compounds 1 to 3 on the sliding resistance. In FIG. 1 and FIG. 2, the vertical axis represents the sliding resistance value (unit: mN). In addition, in FIG. 1 and FIG. 2, the horizontal axis represents Examples and Comparative Examples. That is, the plots on the polygonal line in FIG. 1 represent Example 3 (Ex3), Example 2 (Ex2), and Example 1 (Ex1) from the left. The plots on the polygonal line in FIG. 2 represent Example 3 (Ex3), Example 2 (Ex2), and Example 1 (Ex1) from the left.

represent Example 7 (Ex7), Example 6 (Ex6), Example 2 (Ex2), Example 5 (Ex5), and Example 4(Ex4). In FIG. 1 and FIG. 2, "Com1" represents Comparative Example 1, and "Com2" represents Comparative Example 2.

As can be seen from FIG. 1 and FIG. 2, the injection needles showed a smaller sliding resistance values (piercing resistance values) after zero puncture as compared with the comparative injection needles. Hence, according to the present disclosure, coating agents (injection needles) excellent in the effect of reducing friction (puncture resistance) at puncture are surely obtained. Furthermore, the injection needles showed significantly lower sliding resistance values (piercing resistance values) than the comparative injection needles even after ten punctures. Hence, it is considered that the durability can also be enhanced according to the present disclosure.

In addition, it is considered from FIG. 2A that the injection needles on a surface of which a film was formed with the coating agents 2, 5, and 6 (injection needles 2, 5, and 6) are especially excellent in the effect of reducing the friction (puncture resistance) at puncture. Furthermore, it is considered from FIG. 2B that the injection needles on a surface of which a film was formed with the coating agents 2 and 5 (injection needles 2 and 5) can significantly exhibit an effect of enhancing durability.

The results of the coating 2 (EOG), the coating 3 (high pressure vapor), and the coating 4 (radiation) are not shown in the drawings, but similar results to those of the coating 1 (heating) were obtained. That is, the sliding resistance values (piercing resistance values) (mN) after the injection needles 8 to 14, the injection needles 15 to 21, and the injection needles 22 to 28 punctured a rubber cap 0 time were significantly lower than those of the comparative injection needles 3 to 4, the comparative injection needles 5 to 6, and the comparative injection needles 7 to 8. In addition, the sliding resistance values (piercing resistance values) (mN) after the injection needles 8 to 14, the injection needles 15 to 21, and the injection needles 22 to 28 punctured a rubber cap 10 times were significantly lower than those of the comparative injection needles 3 to 4, the comparative injection needles 5 to 6, and the comparative injection needles 7 to 8.

Hence, it is considered that the piercing properties can be improved and the durability can also be enhanced by the injection needle according to an exemplary aspect. In addition, it is expected from the above results that an exemplary coating agent can exhibit the same levels of lubricity and durability as described above for any medical instruments other than needles.

The present application is based on Japanese patent application No. 2016-253828 filed on Dec. 27, 2016, whose disclosure is entirely incorporated herein by reference.

What is claimed is:

1. A coating agent comprising:
   (1) a polyorganosiloxane represented by the following general formula (1):

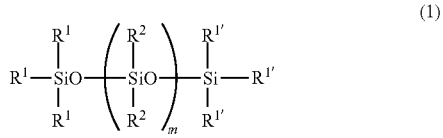

wherein each $R^1$ and each $R^2$ independently represents a monovalent hydrocarbon group,
each $R^{1'}$ independently represents a monovalent hydrocarbon group or a hydroxy group (—OH group), and
m is an integer of 3,500 to 10,000

(2) a polydiorganosiloxane represented by the following general formula (2):

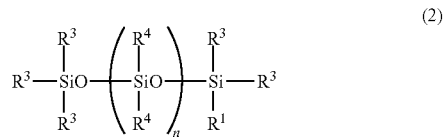

wherein $R^1$ represents a monovalent hydrocarbon group,
wherein each $R^3$ and each $R^4$ independently represents a monovalent hydrocarbon group, and
n is an integer of 30 to 50; and
(3) an amino group-containing polyorganosiloxane or (4) a hydroxy group-containing polyorganosiloxane,
wherein the amino group-containing polyorganosiloxane contains at least one amino group per molecule represented by the following general formula (3):

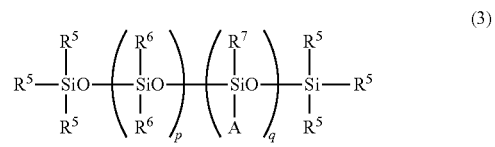

wherein each $R^5$ independently represents a monovalent hydrocarbon group or an —$OR^8$ group, wherein each $R^8$ independently represents a substituted or unsubstituted monovalent hydrocarbon group having 1 to 4 carbon atoms,
each $R^6$ and each $R^7$ independently represents a monovalent hydrocarbon group,
each A independently represents an amino group-containing group,
p:q=5:1 to 100:1, and
q is an integer in a range of 1 to 100;
wherein the hydroxy group-containing polyorganosiloxane is represented by the following general formula (4):

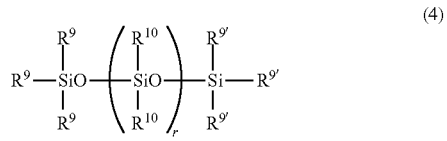

wherein each $R^9$ and each $R^{9'}$ independently represents a monovalent hydrocarbon group or a hydroxy group (—OH), provided that at least one $R^9$ is a hydroxy group (—OH) and at least one $R^{9'}$ is a hydroxy group (—OH),
each $R^{10}$ independently represents a monovalent hydrocarbon group, and
r is an integer of 1,000 to 30,000.

2. The coating agent according to claim 1, wherein each $R^{1'}$ in the general formula (1) independently represents a monovalent hydrocarbon group.

3. The coating agent according to claim 1, wherein the polydiorganosiloxane is contained in a proportion of 40 to 75% by mass based on the total mass of the polyorganosiloxane, the polydiorganosiloxane, and the amino group-containing polyorganosiloxane or the hydroxy group-containing polyorganosiloxane.

4. The coating agent according to claim 1, wherein the polydiorganosiloxane is contained in a ratio by mass of 0.7 to 3.0 relative to the amino group-containing polyorganosiloxane or the hydroxy group-containing polyorganosiloxane.

5. The coating agent according to claim 1, wherein the polyorganosiloxane is contained in a proportion of 2.4 to 5.5% by mass based on to the total mass of the polyorganosiloxane, the polydiorganosiloxane, and the amino group-containing polyorganosiloxane or the hydroxy group-containing polyorganosiloxane.

6. The coating agent according to claim 1, wherein the ratio of m in the general formula (1) to n in the general formula (2) is in a range of 5:1 to 400:1.

7. The coating agent according to claim 1, wherein
in the general formula (1), each $R^1$, each $R^{1'}$, and each $R^2$ is independently a linear or branched alkyl group having 1 to 4 carbon atoms, and
in the general formula (2), each $R^3$ and each $R^4$ is independently a linear or branched alkyl group having 1 to 4 carbon atoms.

8. The coating agent according to claim 1, wherein in the general formula (3), each $R^5$ is independently a linear or branched alkyl group having 1 to 4 carbon atoms, each $R^6$ and each $R^7$ is independently a linear or branched alkyl group having 1 to 4 carbon atoms, and A is a γ-aminopropyl group, a N-(β-aminoethyl)aminomethyl group, or a γ-(N-(β-aminoethyl)amino)propyl group.

9. The coating agent according to claim 1, wherein in general formula (3), p is an integer in a range of 10 to 800.

10. The coating agent according to claim 1, wherein the coating agent comprises the amino group-containing polyorganosiloxane.

11. The coating agent according to claim 10, wherein in the general formula (3), each $R^5$ is a methyl group, each $R^6$ and each $R^7$ is a methyl group, and each A is a γ-(N-(β-aminoethyl)amino)propyl group.

12. The coating agent according to claim 1, wherein the coating agent comprises the hydroxy group-containing polyorganosiloxane.

13. The coating agent according to claim 12, wherein in the general formula (4), one of $R^9$ is a hydroxy group, one of $R^{9'}$ is a hydroxy group, each of the remaining $R^9$ and $R^{9'}$ is a methyl group, and each $R^{10}$ is a methyl group.

14. The coating agent according to claim 13, wherein in the general formula (4), r is an integer in a range of 10,000 to 15,000.

15. A medical instrument, comprising a substrate and a coating formed from the coating agent according to claim 1.

16. The medical instrument according to claim 15, wherein the medical instrument is a needle.

17. A method of producing a medical instrument, the method comprising:
forming a coating film containing the coating agent according to claim 1 on a surface of a medical instrument,
subjecting the coating film to a curing treatment.

18. The method according to claim 17, wherein the curing treatment is performed by heating or irradiating the coating film.

* * * * *